United States Patent
Dasgupta et al.

(10) Patent No.: US 11,592,437 B2
(45) Date of Patent: Feb. 28, 2023

(54) ELECTROCHEMICAL MEASUREMENT OF CREATININE IN SERUM

(71) Applicant: Indian Institute of Science, Bangalore (IN)

(72) Inventors: Pallavi Dasgupta, Bengaluru (IN); Patnam Krishnaswamy, Bengaluru (IN); Vinay Kumar, Sanjaynagar (IN); Navakanta Bhat, Bengaluru (IN)

(73) Assignee: Indian Institute of Science, Bangalore Karnataka (IN)

(*) Notice: Subject to any disclaimer, the term of this patent is extended or adjusted under 35 U.S.C. 154(b) by 398 days.

(21) Appl. No.: 16/802,179

(22) Filed: Feb. 26, 2020

(65) Prior Publication Data
US 2020/0278340 A1     Sep. 3, 2020

(30) Foreign Application Priority Data
Feb. 28, 2019 (IN) .............................. 201941007991

(51) Int. Cl.
| | | |
|---|---|---|
| G01N 33/487 | (2006.01) | |
| G01N 27/327 | (2006.01) | |
| G01N 27/333 | (2006.01) | |
| G01N 33/49 | (2006.01) | |
| G01N 33/493 | (2006.01) | |

(52) U.S. Cl.
CPC ... *G01N 33/48785* (2013.01); *G01N 27/3272* (2013.01); *G01N 27/3275* (2013.01); *G01N 27/3335* (2013.01); *G01N 33/49* (2013.01); *G01N 33/493* (2013.01)

(58) Field of Classification Search
None
See application file for complete search history.

(56) References Cited

PUBLICATIONS

M. Meyerhoff and G.A. Rechnitz, "An Activated Enzyme Electrode for Creatinine", Analytics Chimica Acta, 85(2):p. 277-285, Sep. 1976.*

* cited by examiner

*Primary Examiner* — J. Christopher Ball
(74) *Attorney, Agent, or Firm* — Schwegman Lundberg & Woessner, P.A.

(57) ABSTRACT

Methods and devices for quantifying creatinine in a test sample are provided. The test sample is contacted with a sensing composition to obtain a product comprising a hydantoin-transition metal complex and ammonia. The sensing composition comprises creatinine deaminase and a transition metal salt. The creatinine deaminase enzymatically reacts with creatinine to provide the N-methyl hydantoin and ammonia. The N-methyl hydantoin forms the hydantoin-transition metal complex with the transition salt. A potential difference is applied to the product to measure a current signal provided by the hydantoin-transition metal complex. Concentration of N-methyl hydantoin is obtained based on the measured current signal using a calibration equation. The concentration of N-methyl hydantoin is correlated with concentration of creatinine to quantify the creatinine in the test sample.

20 Claims, 15 Drawing Sheets

(12)  US 11,592,437 B2

ELECTROCHEMICAL MEASUREMENT OF CREATININE IN SERUM

CLAIM OF PRIORITY

This application claims the benefit of priority to Indian Application No. 201941007991, filed Feb. 28, 2019, which application is incorporated by reference as if reproduced herein and made a part hereof in its entirety, and the benefit of priority of which is claimed herein.

TECHNICAL FIELD

The present subject matter relates in general to quantifying creatinine in test samples, and in particular to methods and devices to quantify creatinine electrochemically in test samples.

BACKGROUND

In a laboratory, concentration of creatinine in a test sample is estimated indirectly, for instance, the test sample is enzymatically treated with creatinine deaminase for release of N-methyl hydantoin and ammonia. The released ammonia is correlated with concentration of creatinine in the test sample. Typically, indirect estimation of serum creatinine by measuring ammonia is performed by biosensors which involve a pH sensitive or ammonium ion selective electrode and a potentiometric sensor or Ion Sensitive Field Effect Transistor (ISFET). However, such biosensors suffer from inherent interference from endogenous ammonia level in the test sample, for example, when the test sample is serum.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1A:
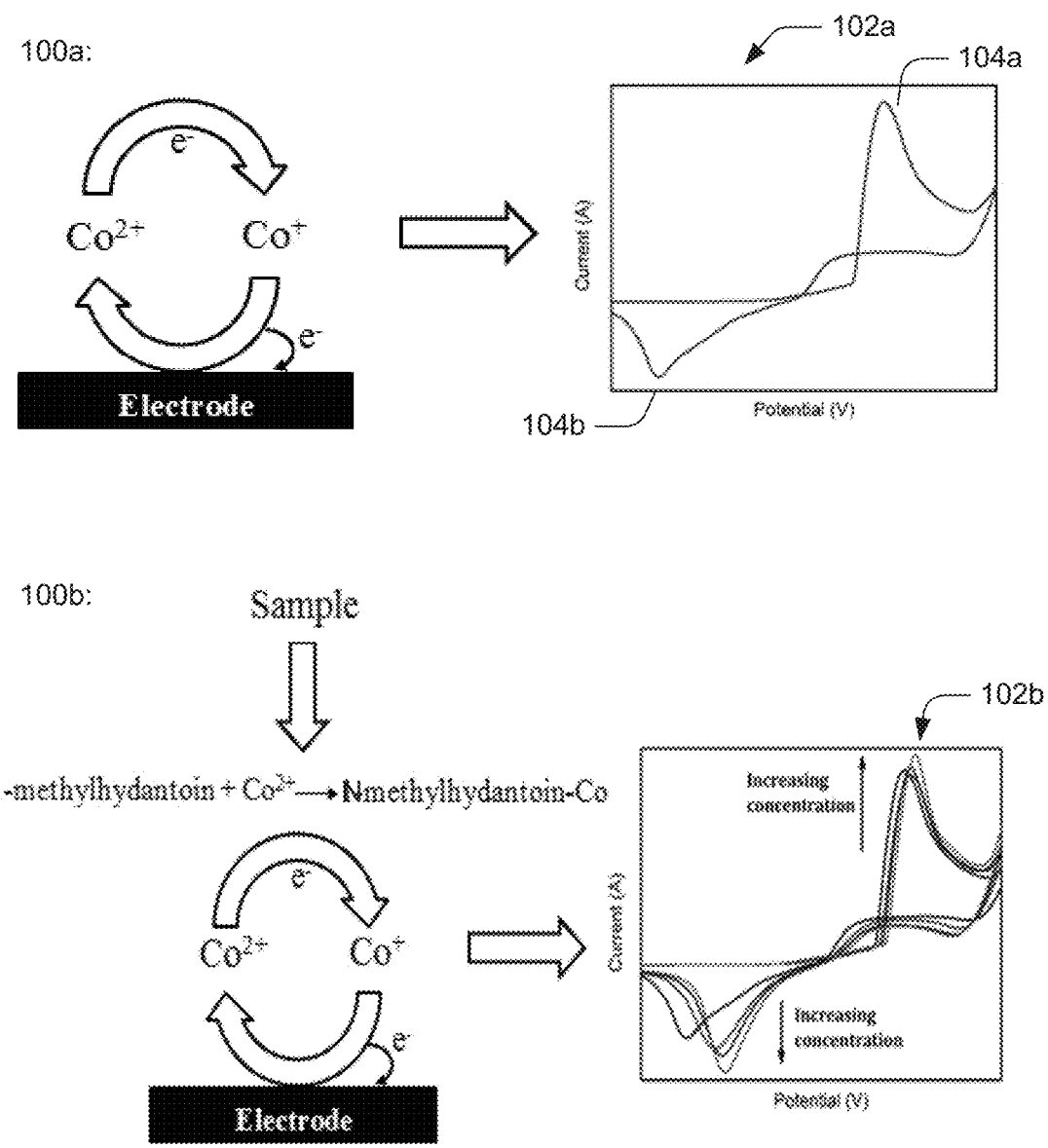
FIG. 1(a) depicts a schematic of electrochemical detection of N-methyl hydantoin, in accordance with an implementation of the present subject matter.

The present subject matter provides methods and devices for quantifying creatinine concentration in a test sample covering the normal physiological range i.e., 0.7-1.2 mg/dL in males and 0.5-1 mg/dL in females and elevations up to higher values, i.e., up to 4 mg/dL in pathological conditions.

Quantification of creatinine, for example, in serum, blood, or urine, can be used for inferring renal efficiency and diagnosis of renal diseases and disorders. Enzymatic degradation of creatinine, by creatinine deaminase to produce N-methyl hydantoin and ammonia, have been used to develop biosensors for quantification of serum creatinine. Such biosensors quantify produced ammonia and correlate the same with analyte, i.e., creatinine to quantify it.

The known biosensors involve a pH sensitive or ammonia ion selective electrode and a potentiometric sensor or Ion Sensitive Field Effect Transistor (ISFET). Response of potentiometric sensor is proportional to the logarithm of the change in concentration of the analyte. Hence, potentiometric sensors are insensitive to lower concentration of creatinine. In case of ISFET based biosensors, fabrication of the same is a complex and expensive process.

The biosensors also use flow-injection systems. Such systems require syringe pumps, and, in some cases, reaction chamber of the biosensors is to be enclosed in polydimethylsiloxane (PDMS) mold which adds to cost and complexity of the quantification. Further, biosensors suffer from inherent interference from endogenous ammonia level in serum which can result in errors.

While biosensors which detect ammonia are available, limited sensors have been developed for quantification of creatinine that rely on the estimation of N-methyl hydantoin. An optical method for N-methyl hydantoin estimation involves its reaction with alkaline ferrocyanide-nitroprusside reagent and monitoring optical density. However, the optical method is subject to errors.

The present subject matter provides methods, compositions, and devices for detection and quantification of creatinine by quantification of N-methyl hydantoin produced via enzymatic degradation of creatinine. The test sample is contacted with a sensing composition comprising creatinine deaminase and a transition metal salt. The creatinine deaminase enzymatically reacts with creatinine to provide N-methyl hydantoin and ammonia.

N-methyl hydantoin reacts with transition metal salt to form a hydantoin-transition metal complex. The hydantoin-transition metal complex is electroactive and provides a current signal on application of a potential difference. The current signal provided by the hydantoin-transition metal complex can be measured.

Concentration of the N-methyl hydantoin can be obtained based on the measured current signal using a calibration equation. The concentration of N-methyl hydantoin can then be correlated with the concentration of creatinine to quantify the creatinine in the test sample. Thus, electroactivity of the hydantoin-transition metal complex can be electrochemically characterized and correlated with concentration of analyte, i.e., creatinine to quantify the creatinine in the test sample.

In one example, in addition to the enzyme, i.e., creatinine deaminase, and the transition metal salt, the sensing composition may also comprise a redox mediator to accelerate kinetics of enzymatic reaction. In one example, the redox mediator is methylene blue.

In one example, the sensing composition comprising creatinine deaminase, the redox mediator, and the transition metal salt may be used for electrochemical measurement of creatinine in a serum, whole blood, or urine as test sample. The test sample may be tested using an electrochemical cell comprising a working electrode, counter electrode, and reference electrode. The sensing composition may be provided in a solution, for example, in a reservoir of the electrochemical cell. In another example, the sensing composition may also be applied or coated on the working electrode of the electrochemical cell.

In one example, the detection of the N-methyl hydantoin, and thereby quantification of creatinine, can be performed using screen-printed electrodes (SPEs). In said example, the sensing composition can be coated on the working electrode of the SPEs, for example, by drop casting and drying the SPEs. In another example, the sensing composition may be provided in a solution in contact with the working electrode prior to contact with the test sample. In SPEs, due to small area available in the working electrode, albumin in the test sample, for example, serum, may interfere with detection of N-methyl hydantoin. The albumin may adhere on the working electrode and affect accuracy of quantification. Hence, in one example, the test sample, i.e., serum may be preprocessed to remove albumin prior to testing.

In another example, a filtration membrane can be provided on the working electrode to filter the albumin from the test sample. In one example, the filtration membrane may be provided on the working electrode prior to the sensing composition. In one example, the filtration membrane may be coated on the sensing composition. The filtration membrane may be one of: a size selective filtration component, a charge specific filtration membrane, or both. The size selective and charge specific filtration membrane may include polymers, such as, polystyrene beads, negatively charged polymer membranes, and combinations thereof. In one example, the negatively charged polymer membrane is sulphonated copolymer, such as sulfonated tetrafluoroethylene-based fluoropolymer-copolymer. It is to be understood that any other polymers may be used with suitable modifications.

The present subject matter provides a reliable electrochemical technique for estimation of serum creatinine by quantification of N-methyl hydantoin produced by enzymatic degradation of creatinine. The present subject matter provides a simple, cost-effective, fast, and accurate method for quantification of N-methyl hydantoin. Further, device fabrication, for example, fabrication of the electrochemical cell and SPEs is easy. The methods and devices of the present subject matter also help in overcoming interference of serum albumin by utilization of the sensing composition with the size selective and charge specific filtration membrane.

The above and other features, aspects, and advantages of the subject matter will be better explained with regard to the following description and accompanying figures. It should be noted that the description and figures merely illustrate the principles of the present subject matter along with examples described herein and, should not be construed as a limitation to the present subject matter. It is thus understood that various arrangements may be devised that, although not explicitly described or shown herein, embody the principles of the present disclosure. Moreover, all statements herein reciting principles, aspects, and examples thereof, are intended to encompass equivalents thereof. Further, for the sake of simplicity, and without limitation, the same numbers are used throughout the drawings to reference like features and components.

FIG. 1(a) depicts a schematic of electrochemical detection of N-methyl hydantoin, in accordance with an implementation of the present subject matter. FIG. 1 depicts two cases, namely, first case 100a and second case 100b to illustrate the working principles of the present subject matter.

In the first case 100a, interaction of the transition metal salt with the working electrode surface is shown in the absence of a biomolecule, such as N-methyl hydantoin. While, cobalt chloride is used as the transition metal salt, however, other transition metal salts may be used as will be understood. Transition metals undergo redox reaction, i.e., they have multiple oxidation states and can undergo electron transfer reactions. When a potential sweep is given to a solution of cobalt chloride taken in an electrochemical cell, cyclic voltammogram as shown in inset 102a was observed.

As shown in inset 102a, cobalt (II) undergoes reduction and provides a reduction peak at point 104a. The reduction peak 104a decays due to diffusion limitation. When the potential is reversed, cobalt (I) gets oxidized and provides an oxidation peak at point 104b.

In the second case 100b, interaction of the transition metal salt with the working electrode surface is shown in the presence of N-methyl hydantoin. When N-methyl hydantoin is introduced in the electrochemical cell, as shown in the second case 100b, the N-methyl hydantoin forms a hydantoin-transition metal complex, in this case, hydantoin-cobalt complex. The hydantoin-cobalt complex is electroactive and provides current signal as can be seen from inset 102b. In particular, from inset 102b, it can be observed that with increase in concentration of hydantoin, concentration of the hydantoin-cobalt complex also increases which consequentially leads to increased current signal. The electroactivity of the hydantoin-cobalt complex, hereinafter also referred to as hydantoin-transition metal complex, can be electrochemically characterized to quantify creatinine.

The hydantoin-transition metal complex may be electrochemically characterized, for example, by using cyclic voltammetry to obtain graph illustrated by inset 102b. The voltage range that is used may be between −1.5 volt to 1 volt. Using the graph obtained by cyclic voltammetry, a potential difference at which hydantoin-transition metal complex provides maximum and stable current response can be obtained. In the example where the transition metal was cobalt, this stable and maximum potential difference was found to be −0.9 V and corresponded to reduction current signal. However, as will be understood, depending on the transition metal, the potential difference and the current signal, whether reduction current signal or oxidation current signal, can vary.

At the stable and maximum potential difference found using the cyclic voltammetry, by using amperometry, a reference graph can be obtained showing a variation of current signal with increasing concentration of N-methyl hydantoin.

From the reference graph, a calibration equation can be obtained. Using the calibration equation, the quantification of hydantoin and, thereby, creatinine can be performed as shown by method in FIG. 1(b). While FIG. 1(b) depicts that a single potential measurement is used for quantifying creatinine in the test sample, a voltage sweep may also be used for quantifying creatinine with suitable modifications, as will be understood.

Figure 1B:
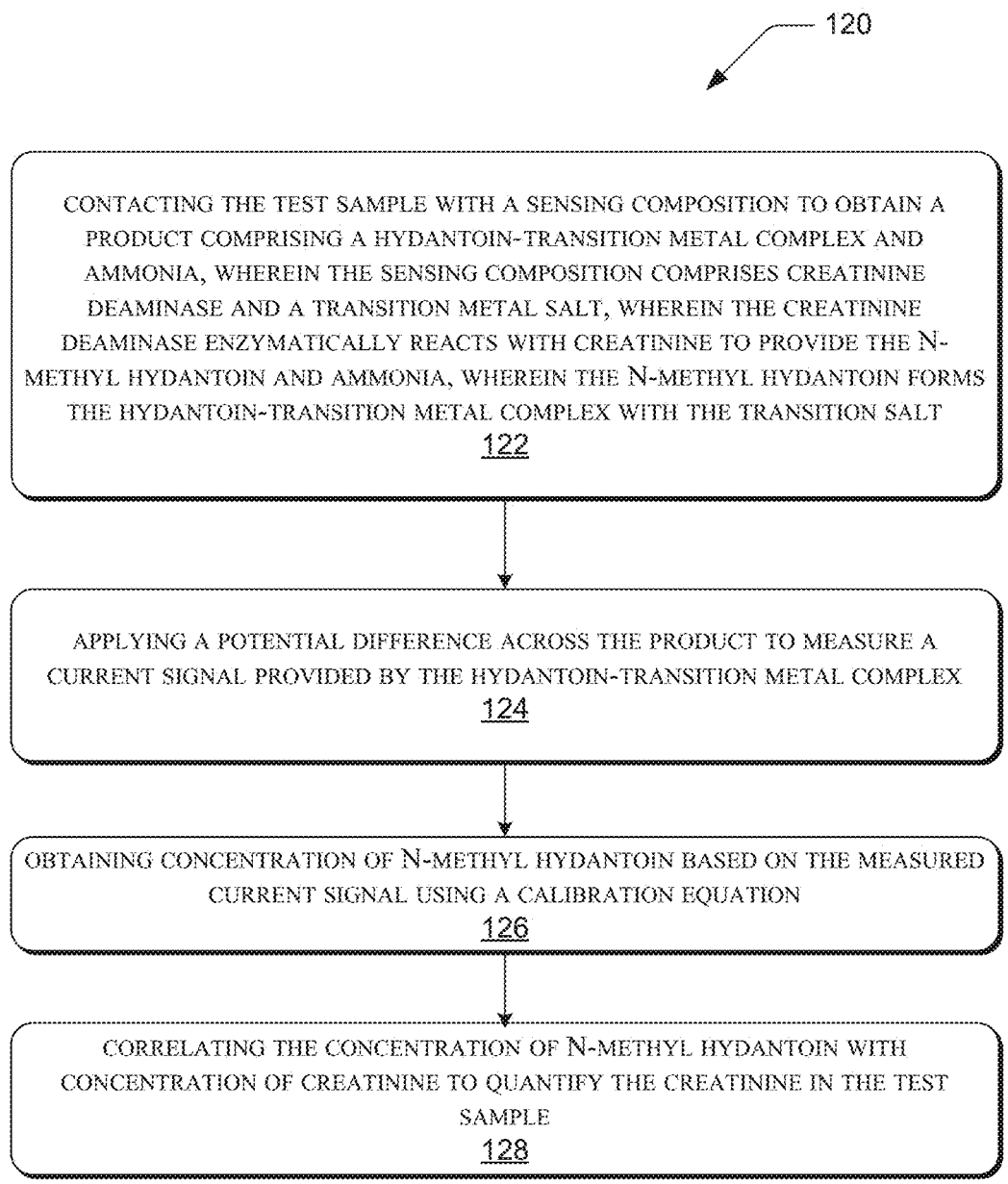
FIG. 1(b) depicts an example method for quantification of creatinine, in accordance with an implementation of the present subject matter.

FIG. 1(b) depicts an example method 120 for quantification of creatinine in a test sample, in accordance with an implementation of the present subject matter. The test sample may be serum, blood, or urine. For the sake of convenience, the method is explained with reference to serum. However, it is to be understood that blood and urine may be used as well.

At block 122, the test sample, such as serum, is contacted with a sensing composition. In one example, the sensing composition may be provided in an electrochemical cell comprising a working electrode, a counter electrode, and a reference electrode. In one example, the working electrode is glassy carbon, counter electrode is platinum plate, and reference electrode is platinum wire. It is to be understood that any other material may also be used to fabricate the electrodes and the predetermined potential may vary according to the material used. The sensing composition may be provided in solution form in a reservoir of an electrochemical cell, in one example. The sensing composition may alternatively be applied or coated on the working electrode of the electrochemical cell. In one example, when the electrochemical cell is used, the sensing composition can comprise creatinine deaminase, the transition metal, and a redox mediator.

The creatinine deaminase is an enzyme which converts creatinine to N-methyl hydantoin and ammonia. The transition metal salt reacts with the N-methyl hydantoin to provide the hydantoin-transition metal complex, the electroactivity of which can be quantified to estimate creatinine. The transition metal salt may be selected from salts having cations selected from the group consisting of iron, cobalt, zinc, copper, and combination thereof. The transition metal salt may be cobalt chloride, ferric chloride, cupric chloride, and combinations thereof. The redox mediator in the sensing composition helps in accelerating kinetics of enzymatic reaction. In one example, the redox mediator used is methylene blue.

In another example, the serum is contacted with the sensing composition on a working electrode of a screen-printed electrode (SPE). The sensing composition may be provided in a solution in contact with the working electrode of the SPE. In another example, the sensing composition may be coated or applied on the working electrode of the SPE. In said example, since the working electrode of SPE provides lesser surface area for assessing electroactivity of the hydantoin-transition metal complex and serum albumin in unprocessed serum can interfere with assessing the electroactivity, a filtration membrane may be provided on the working electrode to filter interfering molecules from the test sample. The filtration membrane may be coated on the working electrode of the SPE prior to providing the sensing composition. In another example, the filtration membrane may be coated on the sensing composition which is coated on the working electrode. The filtration membrane forms an interface or membrane or layer after drying on the working electrode, for example, after drop-casting and drying.

In one example, the filtration membrane is one of: a size selective filtration membrane, a charge specific filtration membrane, and combination thereof. In one example, the size selective filtration membrane is polystyrene beads. In said example, size of the polystyrene beads is in a range of 30-100 nanometers. While the present subject matter has been explained with reference to polystyrene beads as size selective membrane component, any other conducting polymeric bead with a tendency to self-assemble may also be used as the size selective membrane component.

The charge specific filtration membrane may be a negatively charged polymer. In said example, the negatively charged polymer is a sulphonated copolymer, such as sulfonated tetrafluoroethylene-based fluoropolymer-copolymer, for example, Nafion™. As albumin is negatively charged, the negatively charged polymer repels the serum albumin and helps in enhancing the accuracy of characterizing electroactivity of the hydantoin-transition metal complex by negating the effect of albumin.

At block 124, a potential difference can be applied across to the product comprising the hydantoin-transition metal complex to measure a current signal provided by the hydantoin-transition metal complex. The potential difference may be applied, for example, by using a voltage source. As previously explained, the potential difference applied can vary depending on the transition metal salt used in the sensing composition. In one example, when the transition metal salt used is cobalt chloride, the potential difference is −0.9 V. In another example, the voltage source may provide a voltage sweep. Voltage range of the sweep may depend on the transition metal salt used. Further, the current signal that may be measured can be the reduction current signal or the oxidation current signal or both based on the transition metal salt used. In the example where the transition metal salt is cobalt chloride, reduction current signal provided by the hydantoin-transition metal complex may be measured. Further, the current signal measured may depend on the device used for measurement, for example, the reduction current signal may be measured when an electrochemical cell is used and the oxidation current signal may be measured when an screen-printed electrode is used. The current signal can be measured after a reaction time, for example, about 1 minute, elapses to allow for completion of the reaction.

At block 126, concentration of N-methyl hydantoin can be obtained based on the measured current signal using the calibration equation as explained previously. At block 128, the concentration of N-methyl hydantoin may be correlated with the concentration of creatinine to quantify the creatinine in the test sample as the concentration of hydantoin-transition metal complex is directly proportional to the concentration of serum creatinine. As previously explained, the quantification of creatinine by using method 120 can be performed using devices, such as the electrochemical cell or screen-printed electrodes (SPEs).

Figure 2A:
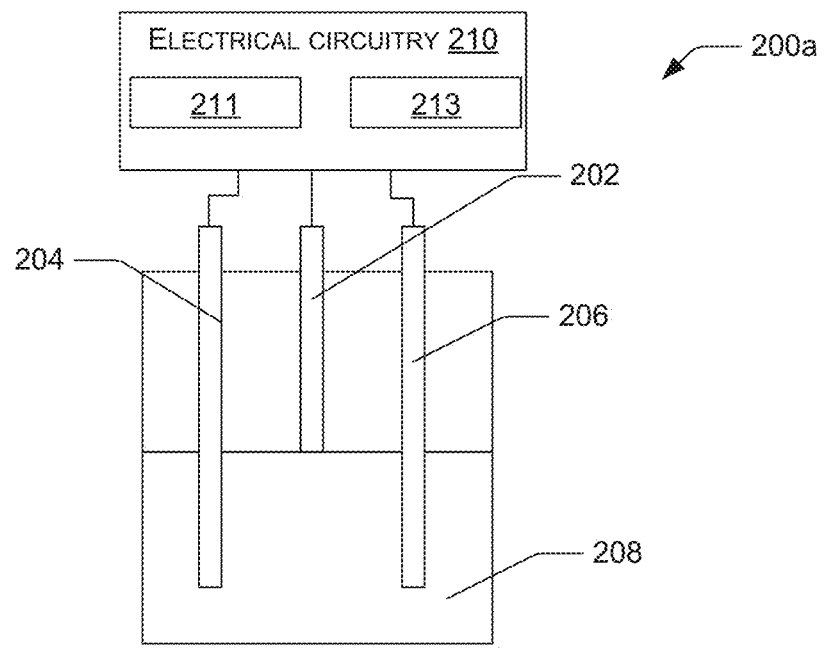
FIG. 2(a) depicts an example electrochemical cell, in accordance with an implementation of the present subject matter.
Figure 2B:
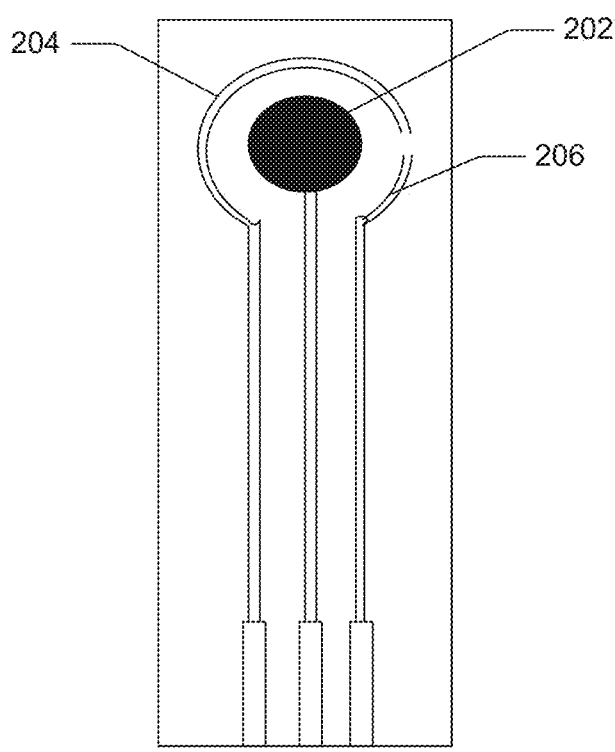
FIG. 2(b) depicts an example screen-printed electrode, in accordance with an implementation of the present subject matter.

FIG. 2(a) and FIG. 2(b) provide schematics of example devices which can be used for quantification of serum creatinine, in accordance with an implementation of the present subject matter. FIG. 2(a) depicts an electrochemical cell 200a and FIG. 2(b) depicts a screen-printed electrode (SPE) 200b, in accordance with an implementation of the present subject matter. Both the electrochemical cell 200a and the SPE 200b may be associated with a voltage source, to apply a potential difference across the electrodes in contact with the reaction product comprising the hydantoin-transition metal complex, and a current sensor, to measure the current signal provided by the hydantoin-transition metal complex on application of the potential difference. In one example, the voltage source may also provide a voltage sweep, i.e., varying potential difference instead of a single potential measurement.

As shown, the electrochemical cell 200a and the SPE 200b can comprise a working electrode 202, a counter electrode 204, and reference electrode 206. With reference to FIG. 2(a), the electrochemical cell 200a can comprise a reservoir 208 and the sensing composition may be provided in a solution in the reservoir 208. In one example, the solution can comprise additional components, such as, saline, buffer, and the like. In another example, the working electrode 202 can have the sensing composition coated on the working electrode 202.

In the electrochemical cell 200a, the sensing composition used can comprise creatinine deaminase, the transition metal salt, and the redox mediator. In one example, reaction volume, which includes the test sample, may be 10 mL. For example, when whole blood is used as test sample, 300 µL of the whole blood may be diluted with saline, buffer, and the like, up to 10 mL to obtain the reaction volume. Further, the reaction volume of 10 mL may comprise the sensing composition having the transition metal salt in a range of 4 mg to 10 mg, the redox mediator in a range of 0.2 mg to 0.5 mg, and the creatinine deaminase in a range of 0.3 µmol/min to 1 µmol/min. In another example, the transition metal salt may be provided in a range of 0.4-0.1% wt/volume of the reaction volume, the redox mediator may be provided in a range of 0.002 to 0.005 wt/volume of the reaction volume, and the creatine deaminase may be provided in a range of 0.3 µmol/min to 1 µmol/min. In one example, the transition metal salt is cobalt chloride and the redox mediator is methylene blue.

For quantification of serum creatinine, processed or unprocessed test sample, namely, serum, blood, or urine, can be contacted with the solution. The electrical circuitry 210 of the electrochemical cell 200a can help in applying and measuring voltage and current for quantification of the creatinine.

The electrical circuitry 210 can include a voltage source 211 coupled to the working electrode 202, the counter electrode 204, and reference electrode 206 to apply a potential difference across the counter electrode 204 and the working electrode 202 that are placed in the reservoir comprising the product hydantoin-transition metal complex. The electrical circuitry 210 can also include a current sensor 213 to measure the current signal provided by the hydantoin-transition metal complex on application of the potential difference.

As will be understood, a computing device having a processor (not shown) may be associated with the electrical circuitry 210. The processor may receive signals corresponding to the applied potential difference from the voltage source 211 and signals corresponding to the current signals measured from the current sensor 213. The processor can perform the computation of obtaining the concentration of N-methyl hydantoin based on the measured current signal and the applied potential difference using the calibration equation and correlating the obtained concentration of N-methyl hydantoin with creatinine to quantify the creatinine in the test sample. In one example, the computing device can also include a memory. The memory may store the calibration equation, data, and the like. The processor can interface with the memory to perform the abovementioned computations and correlations.

FIG. 2(b) depicts the SPE 200b, in accordance with an implementation of the present subject matter. While FIG. 2(b) does not depict the electrical circuitry 210, it is to be understood that SPE 200b is associated with the electrical circuitry 210 similar to electrochemical cell 200a. Further, while a computing device is also not shown, the same may also be provided.

With reference to FIG. 2(b), in the SPE 200b, surface area of the working electrode 202 is orders of magnitude smaller than that of working electrode 202 of the electrochemical cell 200a. For example, the surface area of the working electrode 202 of the SPE 200b may be in a range of 20 $mm^2$ or lesser. As the surface area is smaller, albumin in unprocessed test sample (for example, when the test sample is serum or whole blood) can interfere with accurate quantification of creatinine. This is because albumin interacts with the working electrode 202. In the SPE 200b, for quantification of creatinine, the sensing composition, comprising the creatinine deaminase, transition metal salt, and the redox mediator, can be provided in a solution or can be coated on the working electrode 202. To reduce interference from albumin, a filtration membrane may also be provided on the working electrode 202. While the albumin interacts with the working electrode 202, it does not interact with the sensing composition. The filtration membrane is to prevent the albumin from reaching the working electrode 202 while allowing the hydantoin/electrons to move freely. Hence, the filtration membrane may be provided directly on the working electrode 202 or may be provided on the coated sensing composition to filter interfering molecules, such as albumin, from unprocessed test sample.

The filtration membrane may be one of: a size selective filtration membrane, a charge specific filtration membrane, and combination thereof. The size selective filtration membrane may be polystyrene beads having a diameter about 30-100 nanometers and the charge specific filtration membrane is a negatively charged polymer, such as Nafion™. In one example, both the size selective filtration membrane and the charge specific filtration membrane may be used. For example, the sensing composition may be first coated with the size selective filtration membrane followed by the charge specific filtration membrane. In one example, the size selective filtration membrane followed by the charge specific filtration membrane may be coated on the working electrode 202 prior to providing the sensing composition in a solution drop or coating on the working electrode 202.

Thus, for fabrication, in one example, the sensing composition comprising the creatinine deaminase, the transition metal salt, the redox mediator, can be coated post application of the size selective and charge specific filtration membrane. In this example, a stock solution may be prepared. The stock solution may comprise the sensing composition separately. For example, the stock solution can comprise cobalt chloride range of 4 mg to 10 mg, methylene blue in a range of 0.2 mg to 0.5 mg, creatinine deaminase in a range of 0.3 μmol/min to 1 μmol/min. The size filtration component may be provided as a stock solution of polystyrene beads of about 100 nm size in a range of 0.5 to 1 w/v %. The charge filtration component requires a stock solution of negatively charged polymers in a range of 0.5 to 2 μL of 5 w/w % of negatively charged polymers in water and 1-propanol. In one example, the negatively charged polymer is a sulphonated copolymer, such as sulfonated tetrafluoroethylene-based fluoropolymer-copolymer, for example, Nafion™. In this example, the stock solution can comprise Nafion™ in a range of 1-5 w/w % of Nafion™ in water and 1-propanol.

As previously explained, in the example where the working electrode 202 of the SPE 200b comprises the coating of the sensing composition and a coating of the filtration membrane provided over the sensing composition, the working electrode 202 may be coated by drop casting a volume of 0.5 to 2 μL of the stock solution and drying the working electrode 202. In said example, the stock solution of the sensing composition can be coated by drop casting and drying the working electrode 202. The size selective filtration membrane can be coated by immersing the coated working electrode 202 in the respective stock solution and withdrawing it slowly. The size selective filtration membrane coated working electrode can then be dried. The stock solution of the charge specific filtration membrane can then be drop casted and dried on the size selective filtration membrane coated working electrode.

In another example, for quantification of creatinine using the SPE 200b, the creatinine deaminase, the transition metal salt, and the redox mediator, i.e., the sensing composition, may be coated on the working electrode 202 or may be provided in a solution form post application of the size selective and charge specific filtration membrane, for example, by drop casting and drying. In said example, the working electrode 202 of the SPE 200b may be first coated with the filtration membrane prior to coating or providing the sensing composition at the working electrode 202.

Figure 3A:
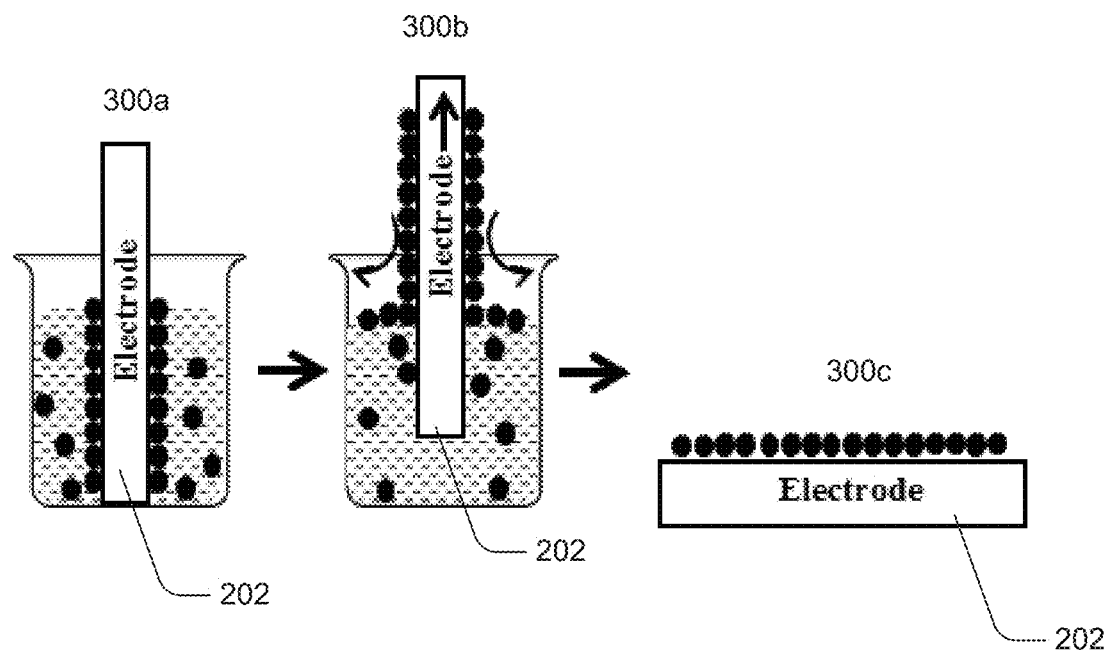
FIG. 3(a) depicts a schematic illustration of formation of polymer beads on electrode surface, in accordance with an implementation of the present subject matter.

FIG. 3(a) depicts a schematic illustration of formation of a monolayer of the size selective filtration membrane on the working electrode, in accordance with an implementation of the present subject matter. FIG. 3(a) is explained with respect to polystyrene beads as an example of the size selective filtration membrane. However, other examples are possible as will be understood. As shown in 300a, the working electrode 202 can be immersed in polystyrene solution, for example, for about 30 second. The working electrode 202 can be withdrawn gradually from the polystyrene solution as shown in 300b. When the working electrode 202 is withdrawn gradually, due to downward pull caused by surface tension and upward capillary force, the polystyrene beads get coated as a layer on the working electrode 202 as shown in 300c. In another example, the negatively, charged polymer may be coated after coating with the polystyrene beads.

Figure 3B:
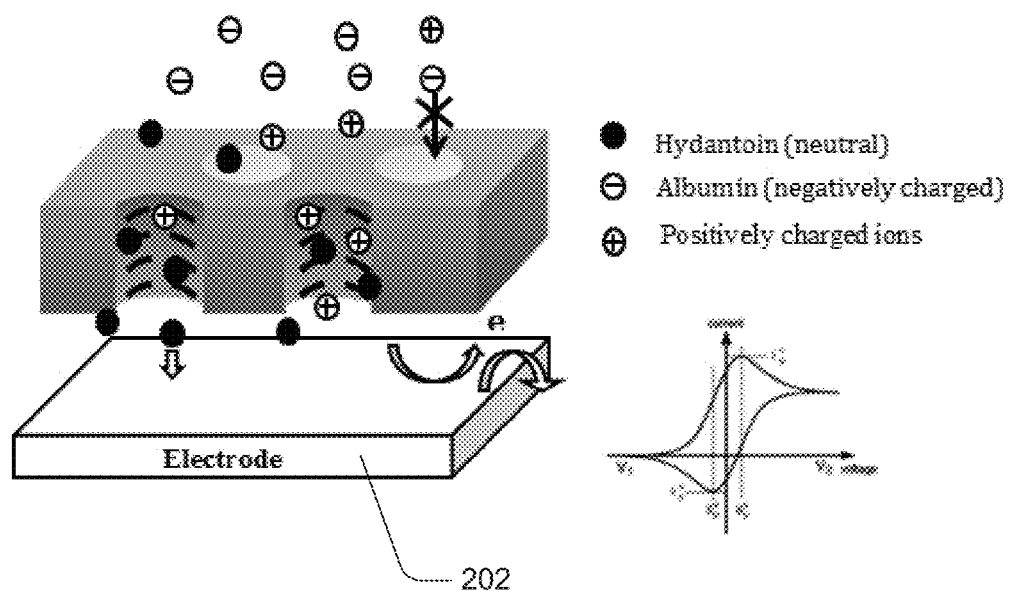
FIG. 3(b) depicts a schematic for minimizing albumin interference during electrochemical detection, in accordance with an implementation of the present subject matter.

FIG. 3(b) depicts a schematic depicting minimization of albumin interference during electrochemical quantification, in accordance with an implementation of the present subject matter. Since albumin is negatively charged polymer, the negatively charged polymer in the filtration membrane repels it and allows hydantoin to pass through its pore for contact with the sensing composition provided on the working electrode 202. While FIG. 3(b) depicts that the negatively charged polymer is Nafion™, any other negatively charged polymer may also be used as will be understood.

The present subject matter, therefore, provides a simple, reliable, and cost-effective electrochemical technique for estimation of serum creatinine. Further, device fabrication, for example, of the electrochemical cell and SPEs is easy. Interference of serum albumin is also reduced, thereby, providing more accurate quantification of creatinine.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Example 1: Cyclic Voltammogram and Variation of Reduction Current

Example 1.1: Transition Metal Salt—Cobalt Chloride

As discussed, cobalt forms a complex with hydantoin. The electrochemical signal of cobalt chloride was directly correlated to its concentration in accordance with the Nernst equation. With increasing hydantoin concentration, cobalt forms a complex with a consequent decrease in its free ionic concentration. The current signal indicates an increasing trend with 1-methyl hydantoin concentration if the complex is electroactive. Electrochemical measurements were performed on CHI 660E workstation.

A typical three electrode cell configuration of an electrochemical cell was used with glassy carbon as the working electrode, platinum as counter electrode and platinum wire as the reference electrode. The total volume of the liquid in the electrochemical cell was fixed at 10 mL. Cobalt chloride solutions were prepared in 0.085 M sodium chloride and physiological levels of sodium chloride, i.e., 0.15 M was used as the buffer for the measurements.

Figure 4A:
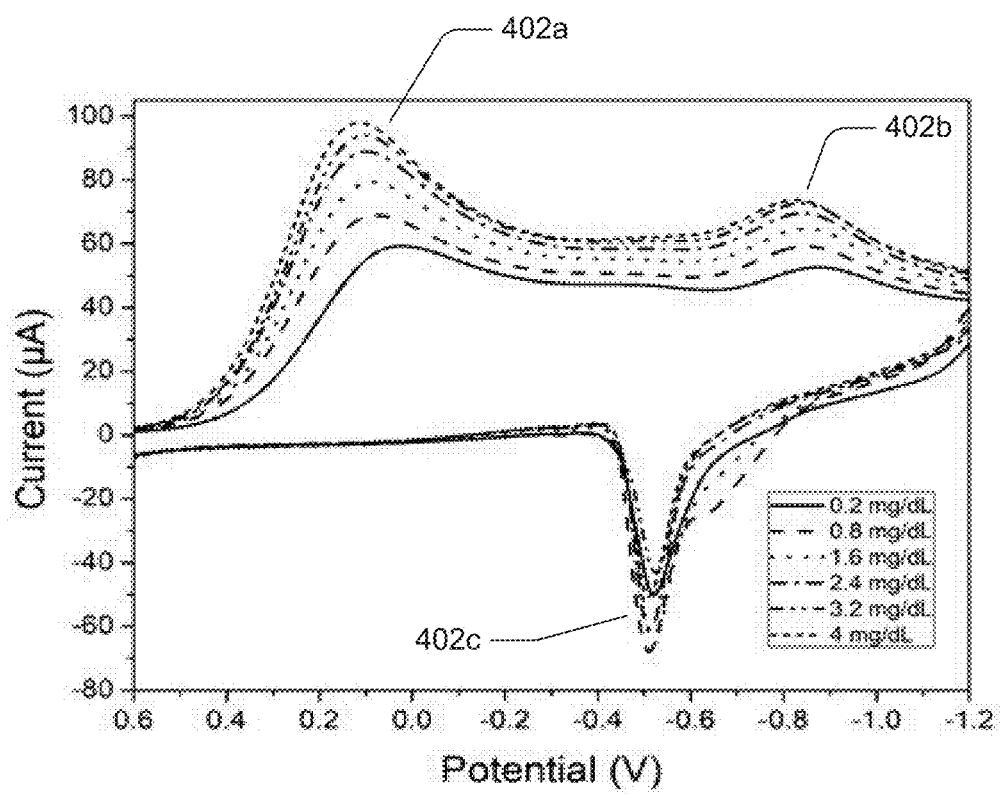
FIG. 4(a) depicts cyclic voltammogram of cobalt chloride for different concentrations of N-methyl hydantoin, in accordance with an implementation of the present subject matter.

Cyclic voltammetry was utilized to study the electron transfer of cobalt chloride and its binding to 1-methyl hydantoin. With reference to FIG. 4(a), cobalt typically exhibits two reduction peaks 402a, 402b and one oxidation peak 402c. The reduction peaks 402a, 402b indicate the conversion of Co (II) to Co(I) and Co (0) while the oxidation peak 402c reflect the conversion of Co(I) to Co(II).

Reduction peak 402b was found to be more consistent and stable and, therefore, in the case of cobalt as transition metal, the potential for future studies was fixed at −0.9V.

Figure 4B:
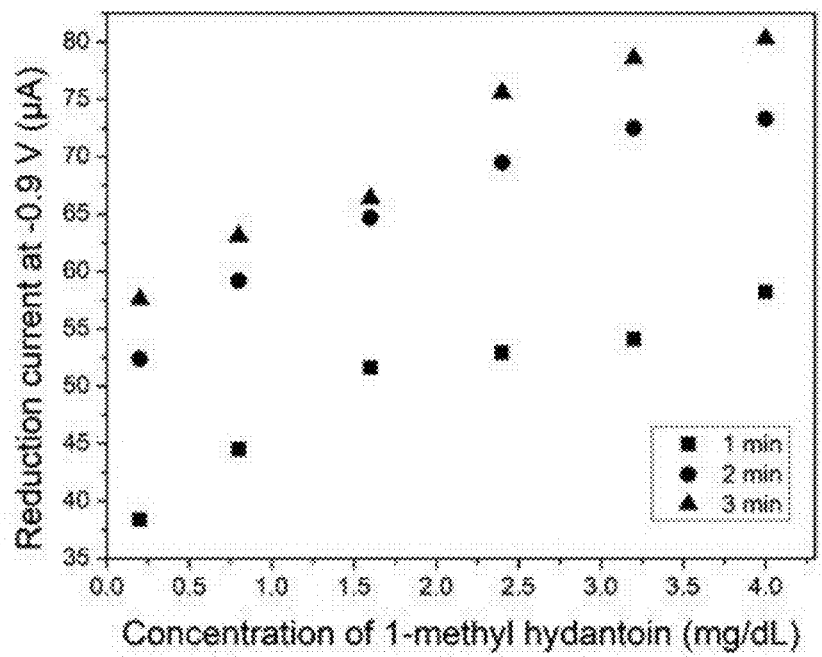
FIG. 4(b) depicts variation of reduction current of cobalt chloride for different concentrations of N-methyl hydantoin, in accordance with an implementation of the present subject matter.

Variation of reduction current of 9 mg cobalt chloride with increasing concentration of 1-methyl hydantoin was studied and the variation was as shown in FIG. 4(b). It was observed that a linearly increasing current signal was obtained with 9 mg of cobalt chloride in presence of increasing concentration of 1-methyl hydantoin from 0.2 to 4 mg/dL.

Figure 4C:
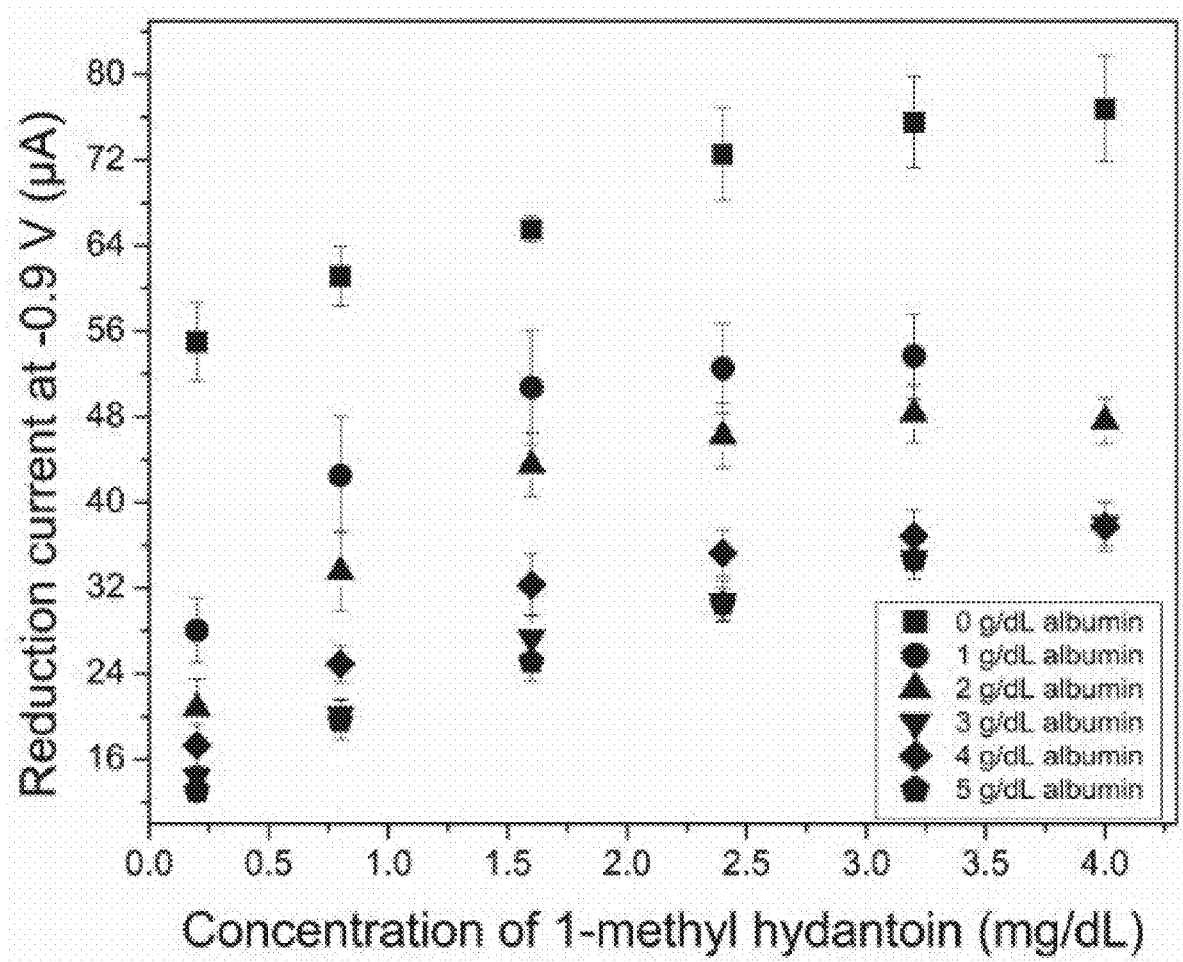
FIG. 4(c) depicts variation of reduction current of cobalt chloride in the presence of albumin, in accordance with an implementation of the present subject matter.

Electrochemical measurements were done in presence of physiological levels of albumin for different concentrations of 1-methyl hydantoin. It was observed that the baseline current did not shift considerably, and the analyte concentration could be quantified from 0.2-4 mg/dL with good resolution as shown in FIG. 4(c). This range covers the physiological concentration of N-methyl hydantoin that would reflect the kidney function.

Figure 4D:
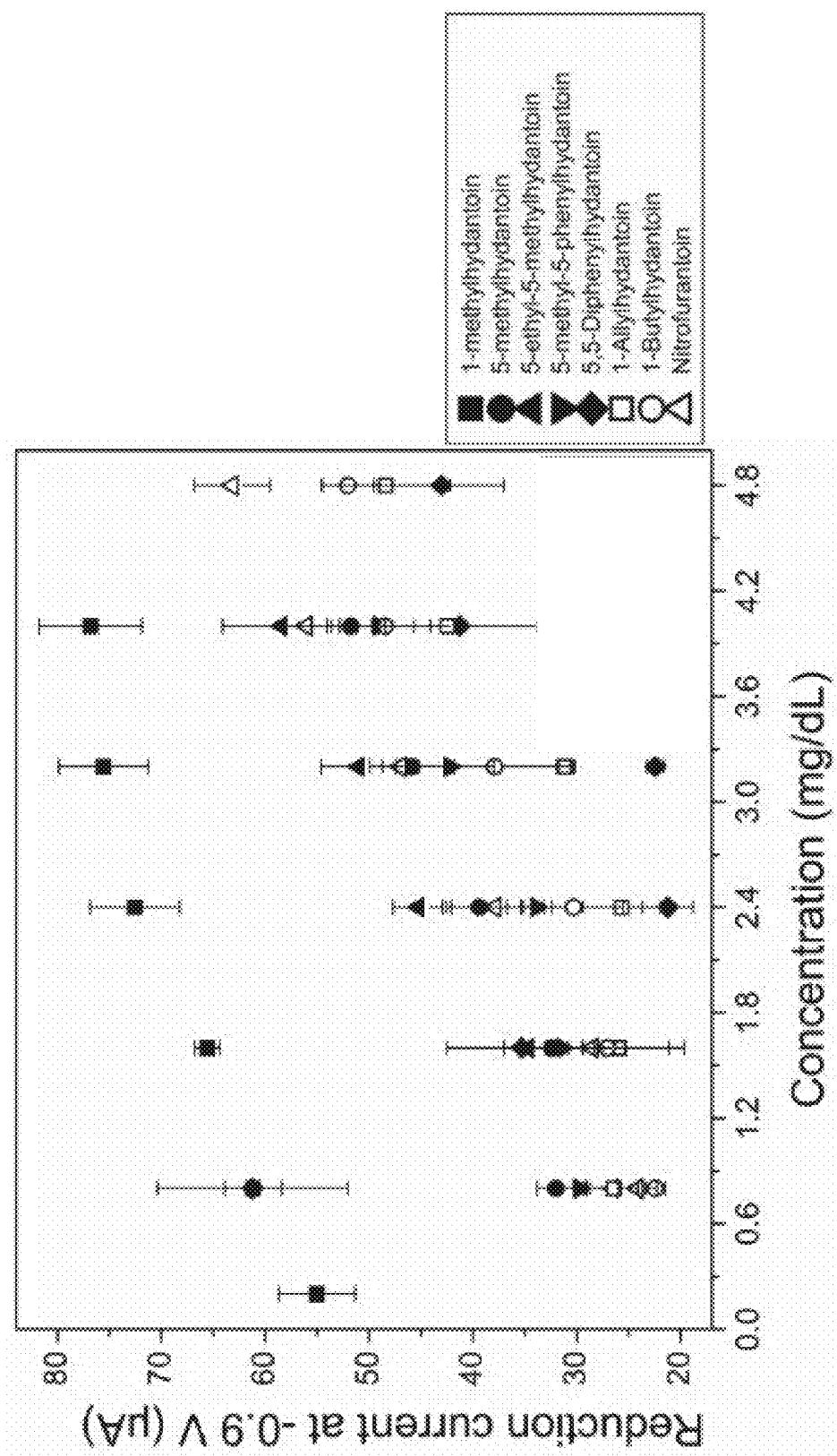
FIG. 4(d) depicts variation of reduction current with increase in concentration of different derivatives of hydantoin, in accordance with an implementation of the present subject matter

Studies were also conducted to test reproducibility of the above results with reference to different derivatives of hydantoin. FIG. 4(d) depicts variation of reduction current with increase in concentration of different derivatives of hydantoin, in accordance with an implementation of the present subject matter. From FIG. 4(d) it can be observed that the sensing composition and the three-electrode cell configuration can be used for detecting and quantifying different derivatives of hydantoin. Further, it was observed that each derivative provided a linearly increasing reduction current signal with increase in its concentration.

Example 1.2: Transition Metal Salt—Ferric Chloride

Figure 4E:
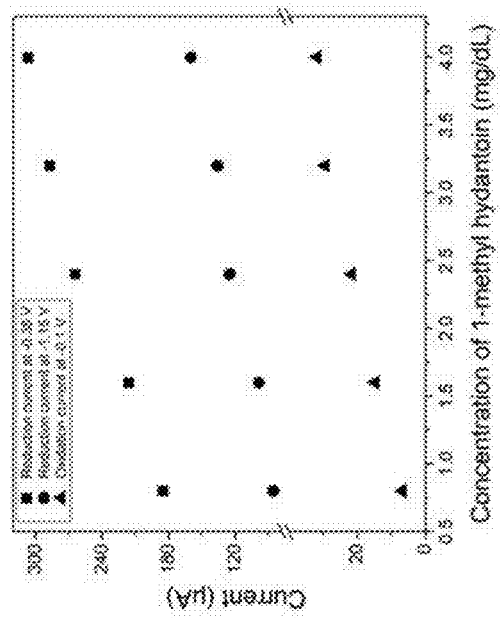
FIG. 4(e) depicts cyclic voltammogram of ferric chloride for different concentrations of methyl hydantoin, in accordance with an implementation of the present subject matter.
Figure 4F:
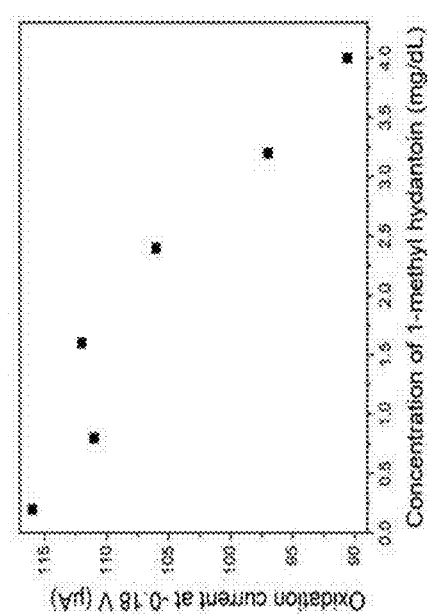
FIG. 4(f) depicts variation of reduction current of ferric chloride for different concentrations of methyl hydantoin, in accordance with an implementation of the present subject matter.

Similar tests as performed with cobalt chloride was also performed with respect to ferric chloride to test binding of hydantoin with iron. FIG. 4(e) depicts cyclic voltammogram of ferric chloride for different concentrations of 1-methyl hydantoin, in accordance with an implementation of the present subject matter. FIG. 4(f) depicts variation of reduction current of ferric chloride for different concentrations of 1-methyl hydantoin, in accordance with an implementation of the present subject matter. It was observed that a linearly increasing current signal was obtained with increasing hydantoin concentration owing to the formation of an electroactive complex of hydantoin and ferric ions.

Example 1.3: Transition Metal Salt—Cupric Chloride

Figure 4G:
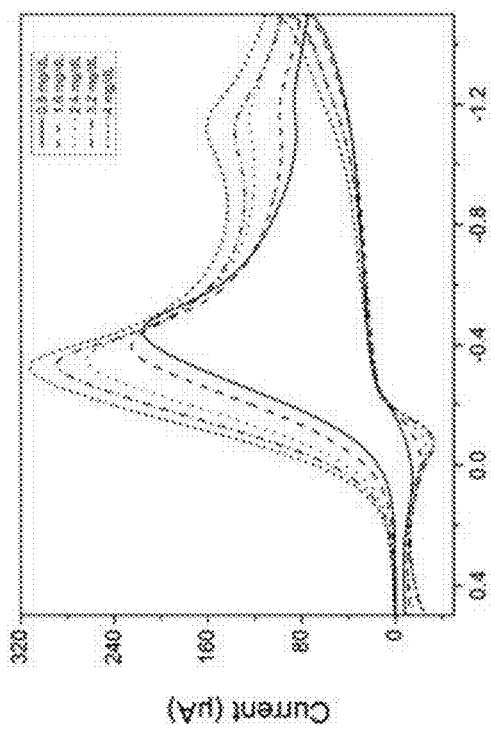
FIG. 4(g) depicts cyclic voltammogram of cupric chloride for different concentrations of methyl hydantoin, in accordance with an implementation of the present subject matter.
Figure 4H:
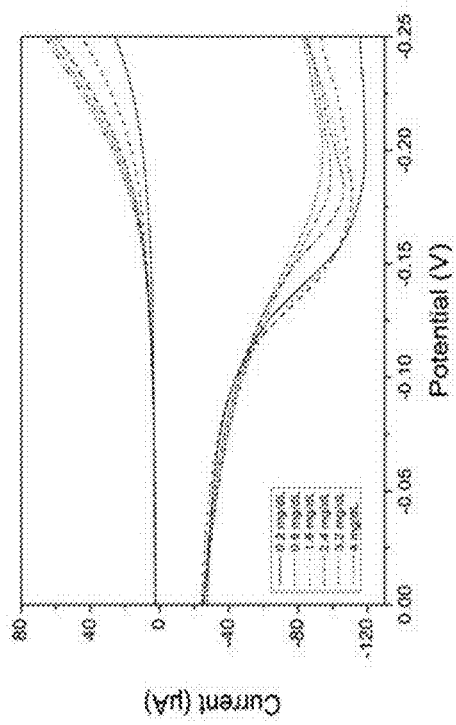
FIG. 4(h) depicts variation of oxidation current of cupric chloride for different concentrations of methyl hydantoin, in accordance with an implementation of the present subject matter.

Similar tests as performed with cobalt chloride and ferric chloride was also performed with respect to cupric chloride to test binding of hydantoin with copper. FIG. 4(g) depicts cyclic voltammogram of cupric chloride for different concentrations of 1-methyl hydantoin, in accordance with an implementation of the present subject matter. FIG. 4(h) depicts variation of oxidation current of cupric chloride for different concentrations of 1-methyl hydantoin, in accordance with an implementation of the present subject matter. The cyclic voltammograms indicated a linearly decreasing oxidation current signal with increasing concentration of hydantoin.

Tests were also performed with respect to zinc chloride and nickel sulphate. In both cases cyclic voltammograms did not change with increasing hydantoin concentration.

Example 2: Determination of Hydantoin from Creatinine

Figure 5A:
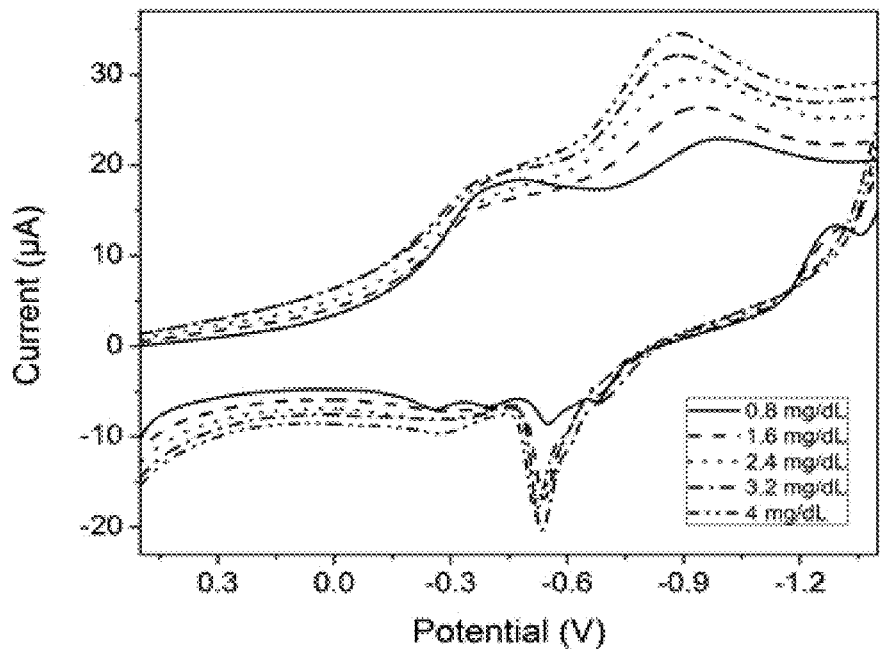
FIG. 5(a) depicts cyclic voltammogram of cobalt chloride for different concentrations of creatinine, in accordance with an implementation of the present subject matter.
Figure 5B:
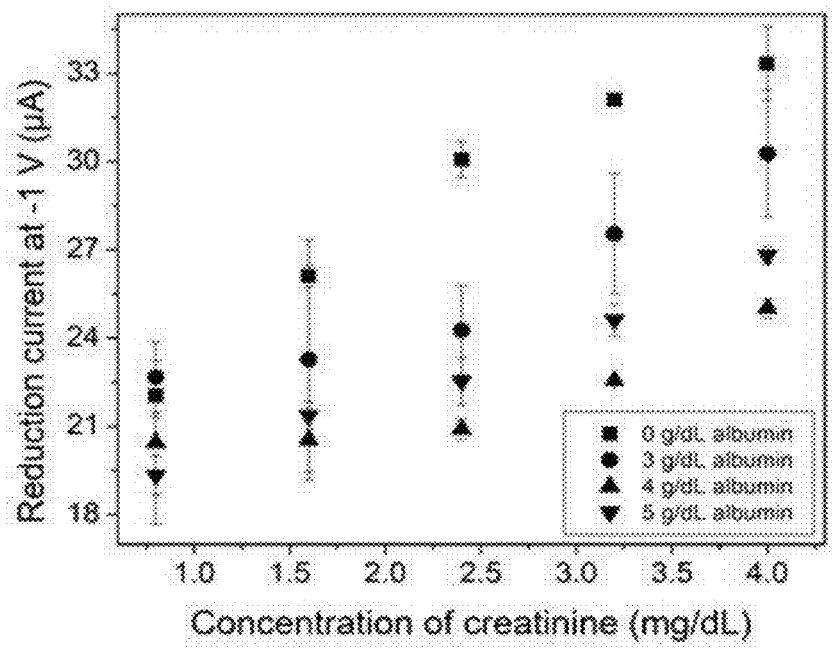
FIG. 5(b) depicts variation of reduction current of cobalt chloride for different concentrations of creatinine in presence or absence of albumin, in accordance with an implementation of the present subject matter.

Determination of 1-methyl hydantoin from creatinine was performed by utilizing the enzyme creatinine deaminase using the electrochemical cell. However, reliable estimation was possible only on introduction of a redox mediator such as methylene blue that accelerates the kinetics of the enzymatic reaction. In this example, the sensing composition comprised 4.5 mg of cobalt chloride, 0.5 mg Methylene Blue and 0.5 μmol/min of enzyme in 10 mL of reaction solution (which included the test sample). FIG. 5(a) depicts cyclic voltammogram of cobalt chloride for different concentrations of creatinine, in accordance with an implementation of the present subject matter. The reduction current increased linearly with increasing creatinine concentration from 0.8-4 mg/dL as shown in FIG. 5(b). The linearity was observed even in presence of physiological levels of serum albumin.

Example 3: Study with Immobilization on Working Electrode

The sensing composition was immobilized directly on the working electrode of the electrochemical cell to make the sensing composition more accessible. This also makes the electrochemical cell more accessible. In this case, 4.5 mg of cobalt chloride, 0.5 mg of Methylene Blue and 0.5 μmol/min of the enzyme was directly immobilized on the surface of the working electrode by drop casting the stock solution on the working electrode surface and subsequently drying in the oven. The electrode was then dried in the oven at 40 deg C. for 20 mins. The modified electrode was then used for electrochemical determination of creatinine.

Figure 6B:
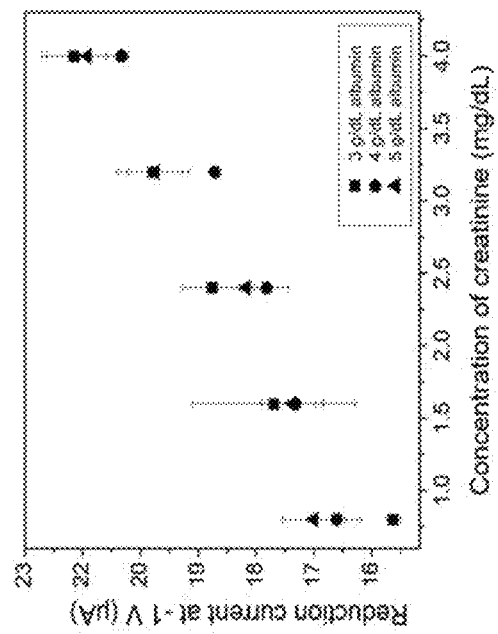
FIG. 6(b) depicts variation of reduction current of cobalt chloride for different concentrations of creatinine using the modified electrode, in accordance with an implementation of the present subject matter.
Figure 6C:
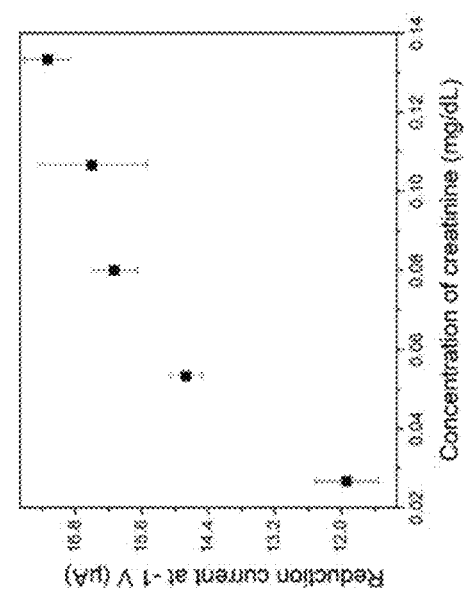
FIG. 6(c) depicts variation of reduction current with increase in concentration of creatinine using whole blood as test sample, in accordance with an implementation of the present subject matter
Figure 6A:
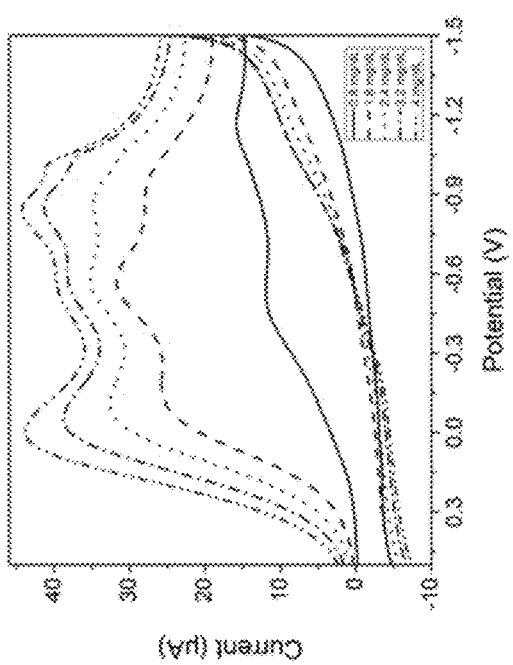
FIG. 6(a) depicts cyclic voltammogram of cobalt chloride for different concentrations of creatinine using a modified electrode, in accordance with an implementation of the present subject matter.

FIG. 6(a) depicts cyclic voltammogram of cobalt chloride for different concentrations of creatinine using the modified electrode, in accordance with an implementation of the present subject matter. FIG. 6(b) depicts variation of reduction current of cobalt chloride for different concentrations of creatinine using the modified electrode, in accordance with an implementation of the present subject matter. A linearly correlated current signal to the creatinine concentration was obtained as shown in FIG. 6(b).

Further, tests were conducted with whole blood as test sample. For this, 300 μL of whole blood sample was taken and diluted up to 10 mL (corresponding to reaction volume in electrochemical cell, as explained previously). The blood sample was spiked with different concentrations of creatinine and detection and quantification was performed using the coated electrode. FIG. 6(c) depicts variation of reduction current with increase in concentration of creatinine using whole blood as test sample, in accordance with an implementation of the present subject matter. A linearly correlated current signal to the creatinine concentration was obtained as shown.

Example 4: Minimizing Interference from Albumin in Serum

Screen-printed electrodes (SPEs) were found to be susceptible to electrode fouling in the presence of serum albumin owing to its non-specific adsorption on the working electrode. This can reduce the active surface area of the working electrode and can lead to current signal attenuation in the presence of albumin. The non-specific adsorption of albumin can be minimized either by sample pre-processing to remove albumin or electrode surface modification.

The latter method is more suitable for developing a point-of-care (POC) device. This has been achieved by three approaches. The first approach involves forming a self-assembled monolayer of polystyrene beads of the order of ~100 nm on the bare SPCE. This shields the electrode from direct contact with albumin. The second approach involves utilization of a charge-selective membrane to repel albumin from the electrode surface. Under physiological conditions, albumin is negatively charged. Hence, Nafion™ was used for the charge-selective membrane as it is a negatively charged sulphonated polymer. A third approach includes using a combination of the polystyrene beads and the negatively charged sulphonated polymer.

Figure 7:
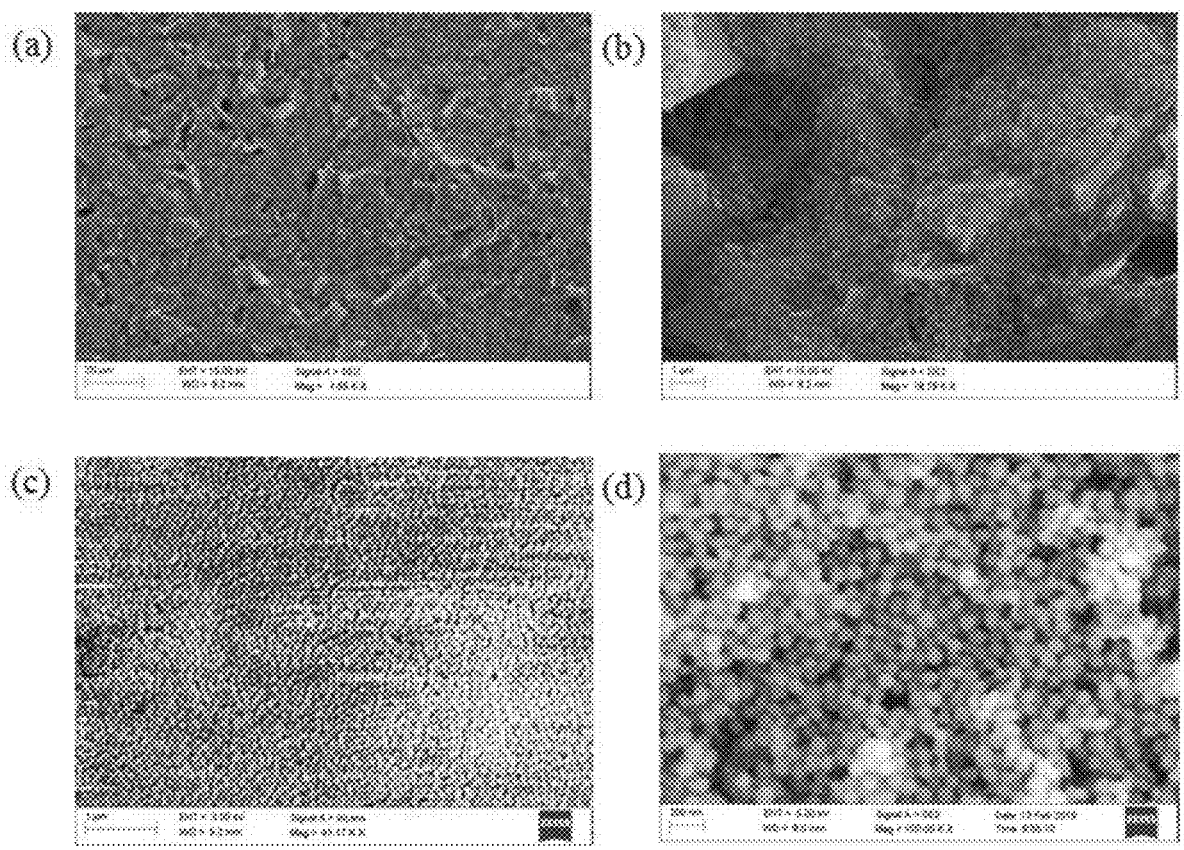
FIG. 7(a) and FIG. 7(b) depict Scanning Electron Microscopy (SEM) images of bare screen-printed electrode at different magnification, in accordance with an implementation of the present subject matter.
FIG. 7(c) and FIG. 7(d) depict SEM image of polystyrene modified electrode at different magnification, in accordance with an implementation of the present subject matter.

FIG. 7(a) and FIG. 7(b) depict Scanning Electron Microscopy (SEM) images of bare screen-printed electrode at different magnification, in accordance with an implementation of the present subject matter. To modify the working electrode using the first approach, a colloidal solution of polystyrene beads of the order of ~100 nm was prepared by mixing 1 mL of 0.5 wt % of a non-ionic surfactant such as Triton with 1.5 mL of 1 wt % of polystyrene beads stock solution. The suspension was sonicated for 30 minutes.

The SPE were vertically immersed in the colloidal solution for 30 seconds and were subsequently withdrawn gradually from the solution. A self-assembled layer was formed on the electrode after drying under ambient conditions due to interplay of capillary forces and surface tension as shown in FIGS. 7(c) and 7(d). FIG. 7(c) and FIG. 7(d) depict SEM images of polystyrene modified electrode at different magnification, in accordance with an implementation of the present subject matter.

To modify the working electrode according to the second approach, the charge specific membrane of Nafion™ was formed on the SPE by directly drop-casting 1 μL of 5 w/w % of Nafion™ stock solution in water and 1-propanol on the electrode. The electrodes were subsequently dried under ambient conditions.

Figure 8:
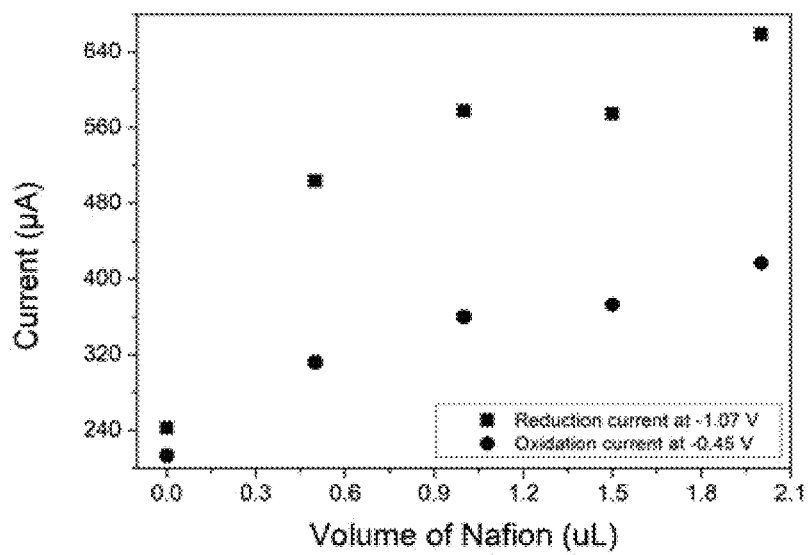
FIG. 8 depicts variation in reduction current of cobalt chloride for Nafion™ modified electrode with different volumes of Nafion™, in accordance with an implementation of the present subject matter.

In one example, volume of Nafion™ was varied. FIG. 8 depicts variation in current of cobalt chloride for Nafion™ modified electrode with different volumes of Nafion™, in accordance with an implementation of the present subject matter. It was observed that the current levels corresponding to reduction and oxidation of cobalt chloride increased with increasing quantity of Nafion™ in the presence of 5 g/dL albumin.

Figure 9:
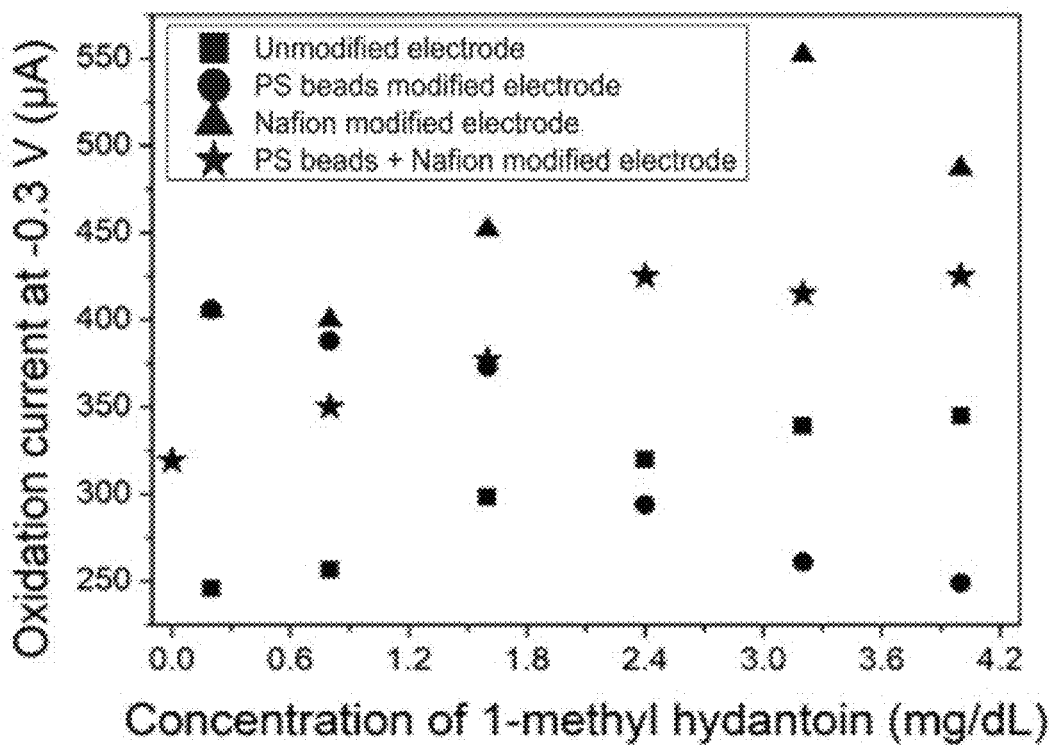
FIG. 9 depicts variation of reduction current of cobalt chloride with bare electrode, polystyrene modified electrode, polystyrene-Nafion™ modified electrode, and Nafion™ modified electrode, in accordance with an implementation of the present subject matter.

Effect of modified electrode, in particular, the effect of unmodified electrode, electrode modified with polystyrene, electrode modified with Nafion™ electrode modified with combination of polystyrene and Nafion™ was studied. In all the cases as described, the electrochemical quantification of hydantoin was ascertained using cobalt chloride in presence of 3 g/dL albumin. FIG. 9 depicts variation of reduction current of cobalt chloride with bare electrode, polystyrene modified electrode, polystyrene-Nafion™ modified electrode, and Nafion™ modified electrode, in accordance with an implementation of the present subject matter.

It was observed that although current increases significantly with Nafion™ modified electrode, however, the linearity of sensing was found to be affected. Electrode modification by Nafion™ alone was found to be suitable for limited concentration range of hydantoin. Further, electrode modified with polystyrene and Nafion™ exhibited linearly correlated current signal over entire physiological range of hydantoin. Depending on the purpose of electrode surface modification, different strategies may be adopted as indicated. For instance, polystyrene modification is suitable to increase the active area of the electrode to an extent while Nafion™ modification is applicable for charge-based segregation of analyte.

Figure 10A:
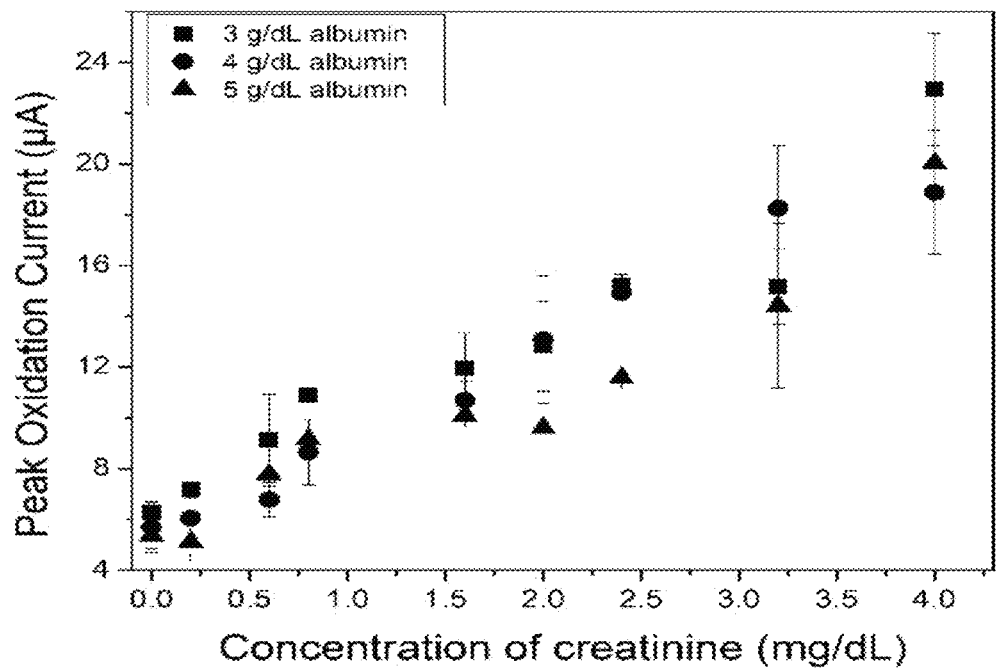
FIG. 10(a) depicts the variation of reduction current at different concentrations of creatinine at different concentrations of albumin, in accordance with an implementation of the present subject matter.

Study was performed using a combination of both the polystyrene and Nafion™ modification on screen-printed electrodes (SPEs). The working electrode was modified by coating it first with the polystyrene beads followed by Nafion™ and subsequently dried. Thereafter, a drop of the sensing composition comprising 0.27 mg cobalt chloride, 0.48 μg methylene blue, 0.02 mg of sodium lauryl sulphate and 0.05 μmol/min of creatinine deaminase was dispensed. 100 μL of test sample, i.e., serum, having different concentrations of creatinine was placed on the working electrode at different concentrations of albumin FIG. 10(a) depicts the variation of reduction current at different concentrations of creatinine at different concentrations of albumin, in accordance with an implementation of the present subject matter. From FIG. 10(a) it was observed that there was a linear correlation between the current signal and concentration of creatinine even at different concentrations of albumin From this, it can be inferred that the polystyrene and Nafion™ modification helped in preventing interference from albumin.

Figure 10B:
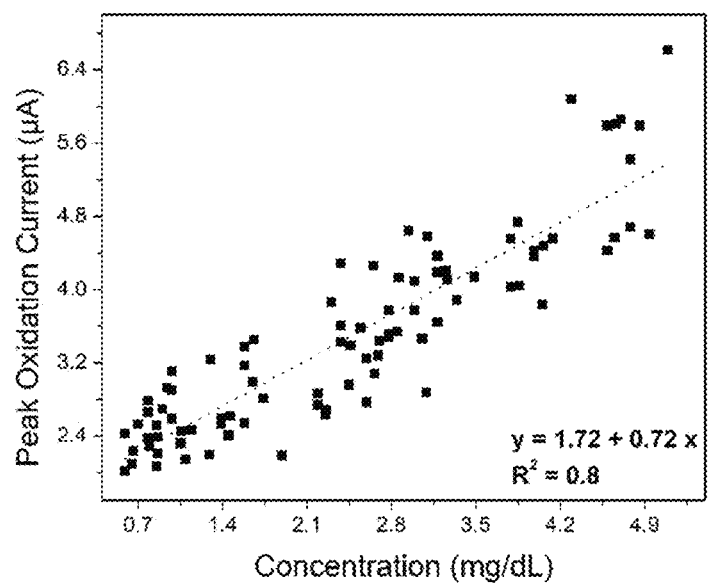
FIG. 10(b) depicts variation of current signal with increases in concentration of creatinine using whole blood as test sample and the modified SPE, in accordance with an implementation of the present subject matter.

Further, efficacy of modified SPE in detecting and quantifying creatinine in whole blood was studied. For this, 30 μL of whole blood sample spiked with different concentrations of creatinine was placed on the modified working electrode of the SPE. FIG. 10(b) depicts variation of current signal with increase in concentration of creatinine using whole blood as test sample and the modified SPE, in accordance with an implementation of the present subject matter. Correlation of determination $R^2$ was found to be 0.8 which indicates positive correlation between the current signal and the concentration of creatinine in the whole blood sample.

Example 5: Study of Effect of Variation in Bead Size and Concentration of Nafion™

Figure 11A:
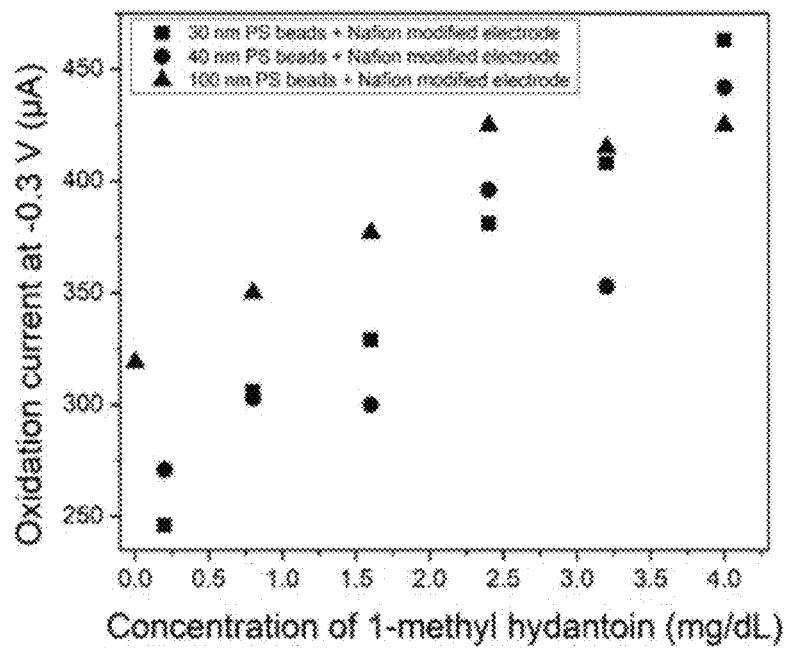
FIG. 11(a) depicts the variation of current signal for different concentration of creatinine obtained using SPEs

In this example, the effect of variation in polystyrene bead size on accuracy of detection and quantification of creatinine in test sample was studied. For this, SPEs modified with different sizes of polystyrene beads (30 nm, 40 nm, and 100 nm) were prepared and modified with Nafion™. 300 µL of the test sample, i.e. serum, spiked with different concentrations of creatinine was placed on the working electrode of the SPE. FIG. 11(a) depicts the variation of current signal for different concentration of creatinine obtained using SPEs modified with different sizes of polystyrene beads, in accordance with an implementation of the present subject matter. It was observed that 30 nm and 100 nm size polystyrene provided better linearity with increase in concentration of creatinine.

Figure 11B:
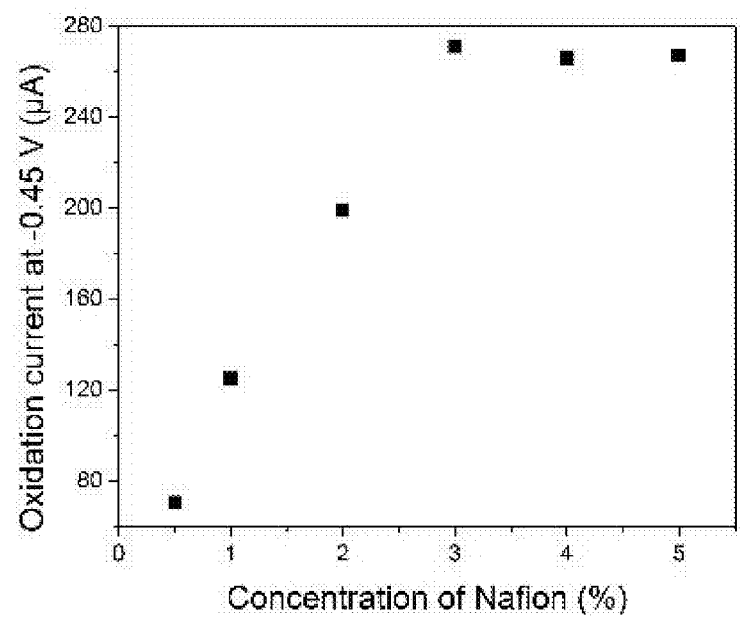
FIG. 11(b) depicts the variation of oxidation current signal with increase in concentration of Nafion™, in accordance with an implementation of the present subject matter.

Further, studies were conducted to determine the effect of varying concentration of Nafion™ on the efficacy of detection and quantification. For this, the sensing composition was coated on the working electrode of the SPE. Nafion™ of different concentrations was drop-cast and dried on the SPEs. The Nafion™ concentration varied from 0.5-3% w/w in water and 1-propanol. Test sample spiked with 5 g/dL of albumin was placed on the SPEs. FIG. 11(b) depicts the variation of oxidation current signal with increase in concentration of Nafion™, in accordance with an implementation of the present subject matter. From FIG. 11(b), it was observed there is a linearity between current signal and concentration of Nafion™ which subsequently forms a plateau beyond 3% w/w.

Figure 11C:
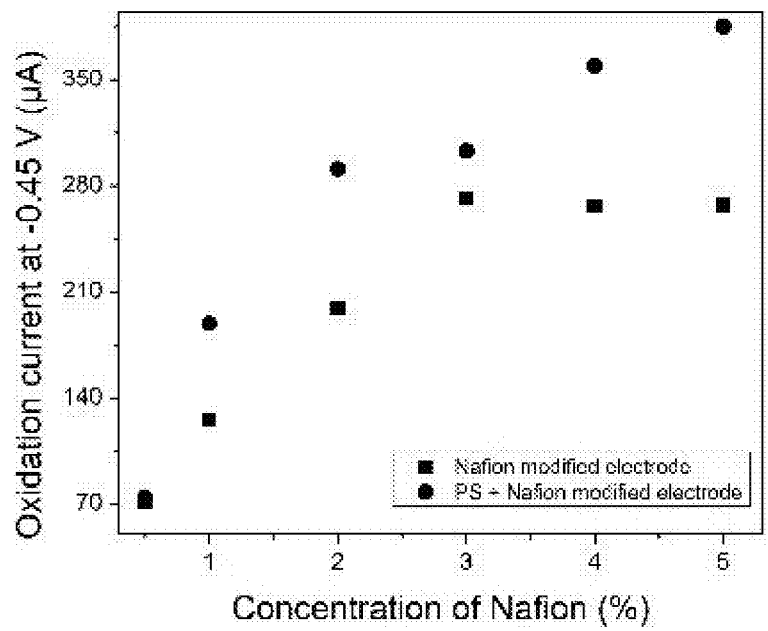
FIG. 11(c) depicts the effect of different Nafion™ concentrations with and without the polystyrene beads, in accordance with an implementation of the present subject matter.

Studies were also conducted to determine the effect of different Nafion™ concentrations with and without the polystyrene beads in the presence of test sample spiked with 5 g/dL of albumin. Range of Nafion™ concentration used for this study was 0.5-5 w/w and the size of polystyrene beads used was about 100 nm. FIG. 11(c) depicts the effect of different Nafion™ concentrations with and without the polystyrene beads, in accordance with an implementation of the present subject matter. From FIG. 11(c) it was observed that the effect of Nafion™ is not evident beyond a concentration of 3% w/w. However, on inclusion of the polystyrene beads, benefits of Nafion™ can be realized over the entire concentration range.

Figure 12A:
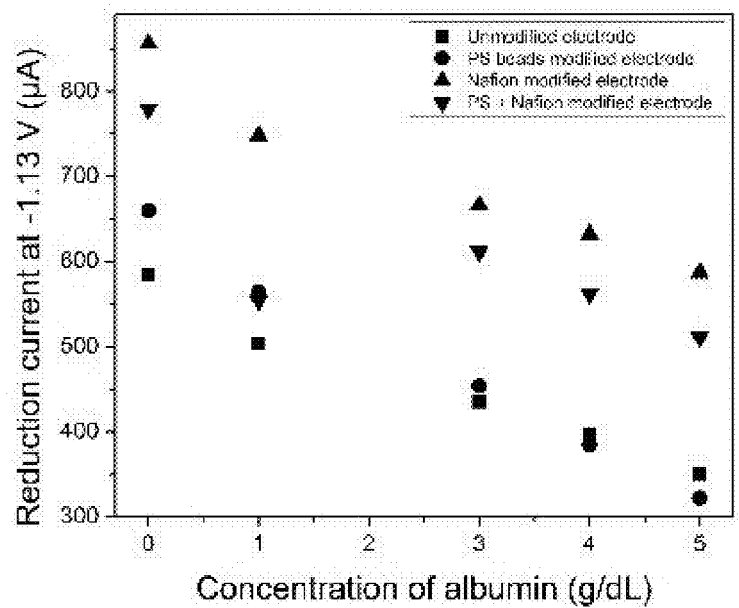
FIG. 12(a) depicts variation in efficacy with different surface modifications at different concentrations of albumin, in accordance with an implementation of the present subject matter.

Example 6: Study of Effect of Surface Modification at Different Concentrations of Albumin In this example, efficacy of SPEs with different surface modifications, namely, unmodified, polystyrene modified, Nafion™ modified, and polystyrene and Nafion™ modified, with varying concentrations of albumin was studied. In said example, the polystyrene beads used had a size of about 100 nm and the Nafion™ concentration used was 5 w/w % in water and 1-propanol. FIG. 12(a) depicts variation in efficacy with different surface modifications at different concentrations of albumin, in accordance with an implementation of the present subject matter.

From FIG. 12(a) it was observed that SPEs with unmodified electrode exhibited maximum signal attenuation with increase in concentration of albumin. In SPEs modified with polystyrene beads, it was observed that the polystyrene beads serve as an effective size filter in the presence of lower concentration of albumin (0-3 g/dL), beyond which it performed like SPEs with unmodified surface with increase in albumin concentration. In SPEs modified with polystyrene and Nafion™ it was observed that the oxidation current signal remained almost unaltered with increase in concentration of albumin.

Figure 12B:
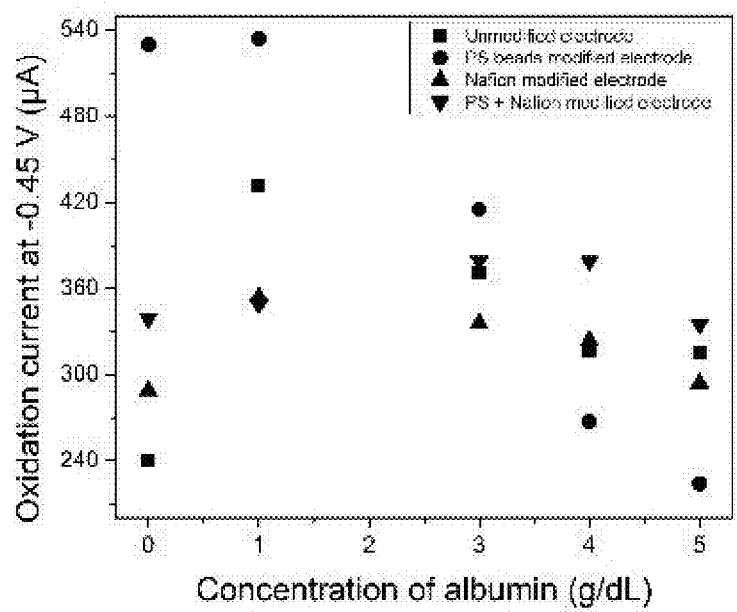
FIG. 12(b) depicts variation in efficacy with different surface modifications at different concentrations of albumin, in accordance with an implementation of the present subject matter.

FIG. 12(b) depicts similar studies performed with respect to reduction current, in accordance with an implementation of the present subject matter. From FIG. 12(b), it was observed that SPEs modified with Nafion™ alone and SPEs modified with polystyrene and Nafion™ provided similar behavior as shown in FIG. 12(a).

The present subject matter, therefore, provides a simple, quick, cost-effective, and reliable electrochemical technique for estimation of serum creatinine using N-methyl hydantoin. The present subject matter covers the normal physiological range of creatinine, i.e., 0.7-1.2 mg/dL in males and 0.5-1 mg/dL in females and elevations up to higher values up to 4 mg/dL in pathological conditions, and hence is more effective than conventional methods. The linearity can be further extended for higher serum concentrations with appropriate dilution.

Although implementations have been described in language specific to structural features and/or methods, it is to be understood that the present subject matter is not necessarily limited to the specific features or methods described. Rather, the specific features and methods are disclosed and explained in the context of a few example implementations.

We claim:

1. A device for quantification of creatinine in a test sample, the device comprising:
    a counter electrode;
    a reference electrode;
    a working electrode;
    a sensing composition for contacting with the test sample, the sensing composition comprising creatinine deaminase, transition metal salt, and a redox mediator, wherein the creatinine deaminase is to enzymatically react with creatinine to form N-methyl hydantoin and ammonia, wherein the N-methyl hydantoin is to form a hydantoin-transition metal complex with the transition salt,
    a voltage source coupled to the counter electrode, the reference electrode, and the working electrode to apply a potential difference across the counter electrode and the working electrode in contact with the hydantoin-transition metal complex; and
    a current sensor to measure a current signal provided by the hydantoin-transition metal complex on application of the potential difference, wherein the measured current signal is usable to obtain a concentration of N-methyl hydantoin, and wherein the concentration of N-methyl hydantoin is correlated with concentration of creatinine to quantify the creatinine in the test sample.

2. The device as claimed in claim 1, wherein the device is an electrochemical cell, wherein the electrochemical cell comprises a reservoir, and wherein the sensing composition is provided in a solution in the reservoir.

3. The device as claimed in claim 1, wherein the device is an electrochemical cell and wherein the sensing composition is coated on the working electrode of the electrochemical cell.

4. The device as claimed in claim 1, wherein the device is a screen-printed electrode (SPE), wherein the working electrode is coated with a filtration membrane to filter interfering molecules from the test sample.

5. The device as claimed in claim 4, wherein the working electrode of the SPE comprises a coating of the sensing composition and a coating of the filtration membrane provided over the sensing composition.

6. The device as claimed in claim 4, wherein the sensing composition is provided in a solution in contact with the working electrode.

7. The device as claimed in claim 4, wherein the filtration membrane is one of: a size selective filtration membrane, a charge specific filtration membrane, and combination thereof.

8. The device as claimed in claim 7, wherein the size selective filtration membrane is polystyrene beads, wherein a size of the polystyrene beads is in a range of 30-100 nanometers.

9. The device as claimed in claim 7, wherein the charge specific filtration membrane is a negatively charged polymer.

10. The device as claimed in claim 9, wherein the negatively charged polymer is a sulphonated polymer.

11. The device as claimed in claim 1, wherein the voltage source is to apply a varying potential difference across the counter electrode and the working electrode (202) in contact with the hydantoin-transition metal complex.

12. A method for quantifying creatinine in a test sample, the method comprising:
contacting the test sample with a sensing composition to obtain a product comprising a hydantoin-transition metal complex and ammonia, wherein the sensing composition comprises creatinine deaminase and a transition metal salt, wherein the creatinine deaminase enzymatically reacts with creatinine to provide the N-methyl hydantoin and ammonia, wherein the N-methyl hydantoin forms the hydantoin-transition metal complex with the transition salt;
applying a potential difference to the product to measure a current signal provided by the hydantoin-transition metal complex;
obtaining concentration of N-methyl hydantoin based on the measured current signal using a calibration equation; and
correlating the concentration of N-methyl hydantoin with concentration of creatinine to quantify the creatinine in the test sample.

13. The method as claimed in claim 12 comprising providing the sensing composition in a reservoir of an electrochemical cell, the electrochemical cell comprising: a working electrode, a counter electrode, and a reference electrode.

14. The method as claimed in claim 12 comprising providing the sensing composition as a coating on a working electrode of a screen-printed electrode (SPE).

15. The method as claimed in claim 12 comprising providing the sensing composition in a solution and contacting the solution with a working electrode of a screen-printed electrode (SPE).

16. The method as claimed in claim 15 comprising providing a filtration membrane coating on the working electrode.

17. A sensing composition for quantifying creatinine in a test sample, the sensing composition comprising creatinine deaminase, a transition metal salt, and a redox mediator.

18. The sensing composition as claimed in claim 17, wherein the sensing composition comprises:
the creatinine deaminase in a range of 0.3 µmol/min to 1 µmol/min;
the transition metal salt in a range of 0.4%-0.1% wt/volume of a reaction volume comprising the test sample; and
the redox mediator in a range of 0.002 to 0.005% wt/volume of the reaction volume comprising the test sample.

19. The sensing composition as claimed in claim 17, wherein the transition metal salt is selected from salts having cations selected from the group consisting of: iron, cobalt, zinc, copper, and combination thereof.

20. The sensing composition as claimed in claim 17, wherein the redox mediator is methylene blue.

* * * * *